United States Patent [19]

Buck

[11] 4,307,077

[45] Dec. 22, 1981

[54] SULFONATED BIS(NAPHTHOXY)ALKANES AS DENTAL PLAQUE BARRIERS

[75] Inventor: Carl J. Buck, Berkeley Heights, N.J.

[73] Assignee: Johnson & Johnson Products Inc., New Brunswick, N.J.

[21] Appl. No.: 172,493

[22] Filed: Jul. 25, 1980

[51] Int. Cl.³ .................. A61K 7/16; C07F 3/06; C07C 143/42
[52] U.S. Cl. .................. 424/56; 260/512 C; 260/429.9; 260/448 R
[58] Field of Search .................. 424/56, 289, 315; 260/429.9, 512 C, 448 R

[56] References Cited

U.S. PATENT DOCUMENTS 3,812,178  5/1974  Weedon .................. 260/512

*Primary Examiner*—Alan Siegel
*Attorney, Agent, or Firm*—Irving Newman

[57] ABSTRACT

Compounds useful in compositions and methods for preventing the attachment of dental plaque to the surfaces of the teeth of mammals comprise certain sulfonated bis(naphthoxy)alkanes and the pharmaceutically acceptable salts thereof. They are used in pharmaceutically acceptable vehicles that are periodically applied to teeth.

5 Claims, No Drawings

4,307,077

SULFONATED BIS(NAPHTHOXY)ALKANES AS DENTAL PLAQUE BARRIERS

TECHNICAL FIELD

This invention relates to certain sulfonated aromatic compounds, oral hygiene compositions comprising the compounds and to methods using such compositions to prevent attachment of bacteria to teeth. More particularly it relates to certain sulfonated bis(naphthoxy)alkanes that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, by fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

Hydrophilic sulfonic acid salt derivatives of certain bis(naphthoxy)alkanes have been synthesized and found to inhibit the deposition of dental plaque onto human teeth. The bis(naphthoxy)alkane sulfonates of this invention are substantially soluble in water or water/organic solvent vehicles and are applied to teeth from various dentifrice formulations, mouth rinses, or other oral hygiene procedures. While the mechanism of action of these sulfonated derivatives in retarding plaque deposition is not known with absolute certainty, it is presumed that films of the anionically charged compounds are deposited on teeth. A mutual repulsion effect is thought to arise between the negatively charged microorganisms responsible for plaque generation and the negatively charged films of bis(naphthoxy)alkane sulfonates. The bis(naphthoxy)alkane sulfonates of this invention are especially effective as components of dentifrices and other oral hygiene preparations in reducing dental plaque deposition on teeth.

A particular feature of the bis(naphthoxy)alkane sulfonates of this invention, which appears to govern their effectiveness as agents for the reduction of plaque deposition, is the balance between the hydrophobic and hydrophilic properties of these compounds. The hydrophobic groups in the bis(naphthoxy)alkane sulfonates are the naphthalene rings, the substituent alkyl groups, and the alkylene linking group [$(CH_2)_n$]. The sulfonate group is the hydrophilic moiety. Accordingly, it has been found expedient to adjust the hydrophobic/hydrophilic balance in the bis(naphthoxy)alkane sulfonates of this invention by independently varying both the size of the hydrophobic alkyl group and the chain length of the alkylene linking group, while maintaining the number of sulfonate groups at two per molecule.

The sulfonated derivatives which are useful for dental plaque control in accordance with the present invention are sulfonated alpha, omega-bis(naphthoxy)alkanes and salts thereof having a structure selected from the group consisting of structure (A),

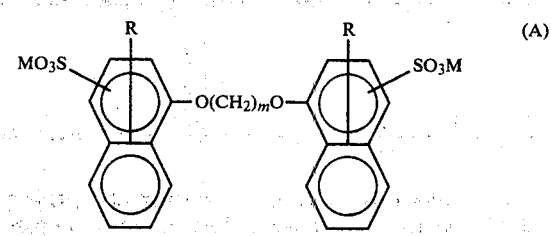

and structure (B),

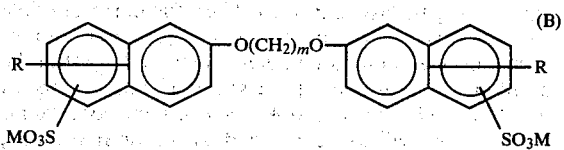

and structure (C),

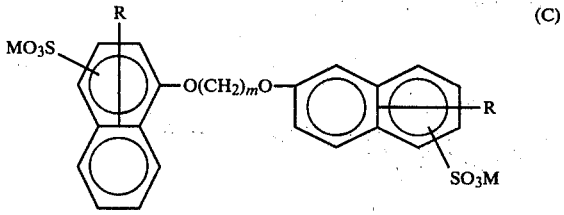

wherein R is hydrogen or a linear or branched alkyl having from 1 to 20 carbon atoms, n is an integer from 2 to 12, M is selected from the group consisting of hydrogen, lithium, sodium, potassium, calcium, magnesium, zinc, aluminum, ammonium and the substituted ammonium ions derived from pharmaceutically acceptable organic amines; provided that R and n are so selected that the weight percent of the sulfonate groups ($SO_3M$) is in the range of about 18% to 35%. Due to the relatively high acidity of the free acids (wherein M is hydrogen) it is preferred that they be converted to the less acidic salts for use in the oral hygiene compositions of this invention. Table 1 illustrates the relationship that must be maintained between the number of carbon atoms in substuent group R and the length (n) of the alkylene linking group in the bis(naphthoxy)alkane sulfonates of this invention in order to achieve the required 18–35% by weight sulfonate group concentration.

TABLE 1

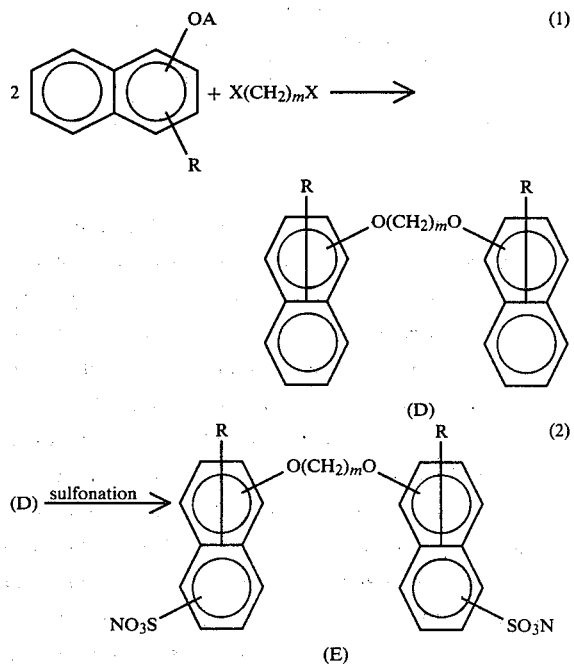

| n | Number of Carbon Atoms in R |
|---|---|
| 2 | 3–20 |
| 4 | 2–20 |
| 6 | 1–20 |
| 8 | 0*–20 |
| 10 | 0*–20 |
| 12 | 0*–20 |

*i.e., R can be hydrogen

The sulfonated alpha, omega-bis(naphthoxy)alkanes of this invention can be synthesized readily by a process consisting of (1) reaction of an alkali metal salt of at least one number selected from the group consisting of 1-naphthol, 2-naphthol and the alkyl substituted derivatives thereof having up to 20 carbon atoms with an alpha, omega-dihaloalkane to afford the corresponding bis(naphthoxy)alkane(s) of structure (D), and (2) aromatic sulfonation of compounds of structure (D) to the disulfonic acid derivatives of structure (E). To obtain the salts of the resulting disulfonic acids, the compounds [of structure (E)] are converted to the desired metal, ammonium, or substituted ammonium salts by neutralization and/or ion-exchange reactions known in the art. The general synthetic sequence for preparation of the disulfonic acid derivatives is shown schematically in equations (1) and (2):

wherein
A = sodium or potassium
X = chlorine, bromine, or iodine.

The 1-naphthol and 2-naphthol required for synthesis of this bis(naphthoxy)alkane intermediates (where R is hydrogen) are readily available items of commerce. The alkyl-substituted naphthols required for synthesis of the other compositions of this invention (where R is an alkyl group) can be synthesized by methods known to those skilled in the art. The position of the alkyl group on the naphthalene ring of the alkylnaphthol is often not known with certainty, but this is of no significance in the practice of this invention. The more significant factors governing the activity of the sulfonated bis(naphthoxy)alkane compounds of this invention as agents for the control of dental plaque deposition are believed to be the balance between hydrophobic and hydrophobic properties of these compounds.

The dihaloalkanes used as co-reactants with the phenolic salts in the synthesis of the bis(naphthoxy)alkanes, according to equation (1), are often readily available items of commerce. If not, they can be synthesized easily by well-known organic reaction processes. Examples of useful dihaloalkanes are 1,2-dibromoethane; 1,4-dibromobutane; 1,5-dichloropentane; 1,6-diiodohexane; 1,8-dibromooctane; 1,10-dibromodecane; and 1,12-dibromododecane.

Sulfonation of the bis(naphthoxy)alkanes can be effected with such reagents as concentrated sulfuric acid, oleum, chlorosulfonic acid and liquid sulfur trioxide. The sulfonations are generally effected in inert solvents, such as methylene chloride, chloroform, and 1,2-dichloroethane; at temperatures of 40° C. or below; and using at least two moles of the sulfonation agent per mole of bis(naphthoxy)alkane. The preferred sulfonation agents are chlorosulfonic acid and liquid sulfur trioxide.

The position of sulfonation on the phenyl rings of the bis(naphthoxy)alkane intermediates is generally not known with certainty and, in any event, is not considered important in the practice of this invention. The structures of the disulfonic acid and disulfonate salt compounds of this invention can be characterized by a number of known methods: (1) NMR and IR spectroscopic analysis, (2) acidimetric assays (on the sulfonic acid derivatives), (3) metal salt analysis via atomic absorption, and (4) elemental analysis.

The alkali metal salts of the sulfonated bis(naphthoxy)alkanes are conveniently prepared by neutralization of a water or alcohol solution of the sulfonic acid derivative with alkali metal hydroxide solutions to the potentiometric endpoint. The salts are recovered by filtration, solvent stripping, or freeze drying, depending on the type of solvent used and whether the salt precipitates directly from the solvent medium. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or are isolated by solvent stripping.

Multivalent metal salts, such as the calcium, magnesium, zinc, and aluminum salts, of the sulfonated products are prepared by methods similar to those described above. In an alternate procedure, multivalent metal salts can be prepared by an ion-exchange reaction between the multivalent ion and either the free sulfonic acid or an alkali metal sulfonate derivative. Ammonium salts of the sulfonic acid derivatives can be prepared by direct addition of ammonia or a primary, secondary, or tertiary organic amine.

The hydrophilic sulfonates of this invention are highly effective in reducing the deposition of plaque during in vitro testing when a suitable balance of hydrophobic and hydrophilic properties is provided in accordance with the foregoing definitions for structures (A), (B) and (C).

The presently preferred in vitro test procedure employed for determining the antiplaque activity of test materials begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects.

EXAMPLE 1

1,8-Bis (1-naphthoxy) octane

A solution of sodium ethoxide was prepared by addition of 2.8 g (0.12 mole) sodium metal to 50 ml. absolute ethanol with stirring and under nitrogen. When all of the sodium had dissolved, a solution of 17.3 g (0.12 mole) 1-naphthol in 15 ml. ethanol was added at once and the mixture heated to reflux. To the black solution was added, over 20 minutes, 13.6 g (0.05 mole) 1,8-dibromooctane. After refluxing an additional 17 hours, 50 ml. boiling water was added and the suspension of solids cooled to room temperature, filtered, washed well with water and ethanol, and dried to give 18.3 g of crude product melting at 60° C. The solids were dissolved in 60 ml. toluene and chromatographed on a column of 183 g silica gel, grade 950. Elution with toluene gave 16.6 g of product. Recrystallization from hexane in the cold gave two crops of purified 1,8-bis(1-naphthoxy) octane weighing 10.7 g, m.p. 61°-64° C., and 2.7 g, m.p. 62°-63° C., as off-white solids.

EXAMPLE 2

Disodium 1,8-Bis(4-sulfo-1-naphthoxy) octane

A solution of 6.9 g (0.0173 mole) 1,8-bis (1-naphthoxy) octane (Example 1) in 70 ml. dry chloroform was maintained at 5°-15° C. during addition of 5.4 g (0.046 mole) chlorosulfonic acid in 7 ml. chloroform over about one hour. After stirring another 17 hours at room temperature, the solids were filtered and washed with chloroform to give 10.0 g (100% theory) of the disulfonic acid derivative.

A solution of 5.5 g of the disulfonic derivative in 100 ml. methanol was neutralized from pH 2.0 to pH 7.1 with methanolic sodium hydroxide. Filtration of the solids and washing with methanol gave 4.8 g of disodium 1,8-bis(4-sulfo-1-naphthoxy) octane as off-white solids. The NMR and IR spectra were consistent with the structure.

EXAMPLE 3

1,8-Bis (2-naphthoxy) octane

Using the method described in Example 1, the crude solids were prepared using 5.5 g (0.24 gram atoms) sodium metal, 34.6 g (0.24 mole) 2-naphthol, and 27.2 g (0.100 mole) 1,8-dibromooctane. Recrystallization from ethyl acetate gave 30.0 g, mp 128° C., and 0.8 g, mp 125°-126° C., of pure 1,8-bix (2-naphthoxy) octane. The NMR spectrum was consistent with the structure and showed the absence of impurities.

EXAMPLE 4

Disodium 1,8-Bis (sulfo-2-naphthoxy) octane

A solution of 19.9 g (0.05 mole) 1,8-bis (2-naphthoxy) octane (Example 3) in 200 ml. dry chloroform was stirred under nitrogen at 26°-30° C. during addition, over 1.5 hours, of 13.4 g (0.115 mole) chlorosulfonic acid in 15 ml. chloroform. After stirring at room temperature for another 21 hours, the suspension was diluted with 100 ml. chloroform and filtered. The solids were washed with chloroform and hexane to give 16.0 g, mp 126°-129° C., and 3.7 g, mp 136°-140° C., of the disulfonic acid derivative.

A stirred suspension of 4.9354 g of the disulfonic acid derivative fraction (melting at 126°-129° C.) in 100 ml. water was neutralized from pH 1.4 to pH 7.8 by addition of 36.0 ml. 0.520 N methanolic aosium hydroxide. The suspension was solvent stripped to afford 4.8 g of disodium 1,8-bis (sulfo-2-naphthoxy) octane as white solids. NMR analysis of the disulfonic acid precursor was consistent with the structure and indicated that the positions of sulfonation were in the 6- and/or 7- position of the naphthalene ring.

EXAMPLE 5

1,12-Bis(1-methyl-2-naphthoxy) dodecane

Using the method of Example 1, the sodium salt of 2-hydroxy 1-methylnaphthalene can react with 1,12-dibromododecane to afford 1,12-bis(1-methyl-2-naphthoxy) dodecane.

EXAMPLE 6

Disodium 1,12-Bis(sulfo-1-methyl-2-naphthoxy) dodecane

Sulfonation of the product from Example 5 with liquid sulfur trioxide in methylene chlorlde as solvent can be effected to yield, after neutralization of the intermediate disulfonic acid with sodium hydroxide, the disodium 1,12-bis(sulfo-1-methyl-2-naphthoxy) dodecane product.

EXAMPLE 7

Dipotassium 1,2-Bis(octadecyl-1-naphthoxy) ethane

In a manner similar to Example 1, 1,2-bis(octadecyl-1-naphthoxy) ethane can be prepared from 1-hydroxy octadecylnaphthalene and 1,2-dichloroethane. Sulfonation can be effected according to the method of Example 2 to afford the disulfonic acid derivative which, after neutralization with alcoholic potassium hydroxide, is converted to dipotassium 1,2-bis(octadecyl-1-naphthoxy) ethane.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A

| Mouthwash Solution | |
|---|---|
| Barrier Agent | 0.5–2.0% w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B

| Mouthwash Solution | |
|---|---|
| Plaque Barrier Agent | 0.5–3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |

EXAMPLE B-continued

| Mouthwash Solution | |
|---|---|
| | 100.0 |

EXAMPLE C

| Abrasive Dentrifice Gel | |
|---|---|
| Plaque Barrier Agent | 2.0–10.0% w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D

| Chewing Gum | |
|---|---|
| Plaque Barrier Agent | 1.0–11.0% w/w |
| Gum Base | 21.3 |
| Sugar | 48.5–58.5 |
| Corn Syrup (Baume 45) | 18.2 |
| Flavors | 1.0 |
| | 100.0 |

EXAMPLE E

| Nonabrasive Gel Dentifrice | |
|---|---|
| Plaque Barrier Agent | 0.05–30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w |
|---|---|
| Distilled Water | q.s. |
| Sodium Saccharin (sweetnener) | 0.20 |
| Sodium Benzoate (preservative) | 0.30 |
| FD&C Blue #1 (0.1% aq. soln.) | 0.27 |
| D&C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| Plaque Barrier Agent | 5.00 (dry basis) |
| Flavor | 0.80 |
| | 100.0 |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

I claim:

1. A sulfonated alpha, omega-bis(naphthoxy)alkane having a structure selected from the group consisting of structure (A),

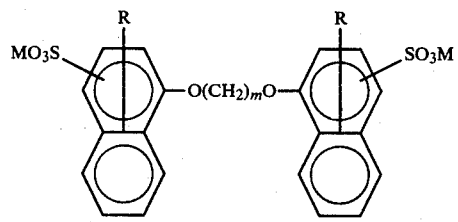

and structure (B),

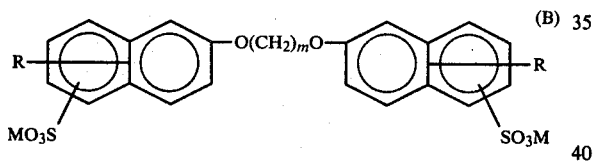

and structure (C),

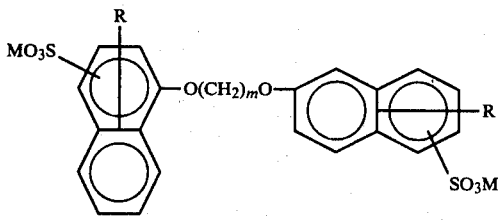

wherein R is hydrogen or a linear or branched alkyl having from 1 to 20 carbon atoms, n is an integer from 2 to 12, and M is selected from the group consisting of hydrogen, lithium, sodium, potassium, calcium, magnesium, zinc, aluminum, ammonium and the substituted ammonium ions derived from pharmaceutically acceptable organic amines; provided that R and n are so selected that the weight percent of (SO3M) the groups is in the range of about 18% to 35%.

2. An oral hygiene composition comprising an effective amount for preventing attachment of dental plaque to teeth of a sulfonated alpha, omega-bis(naphthoxy)alkane having a structure selected from the group consisting of structure (A),

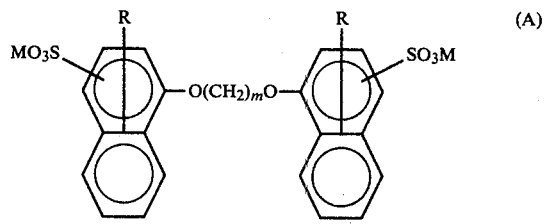

and structure (B),

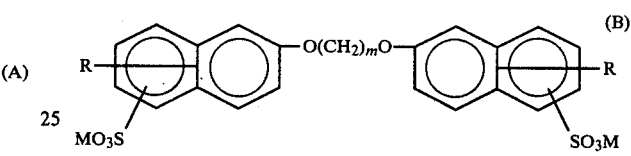

and structure (C),

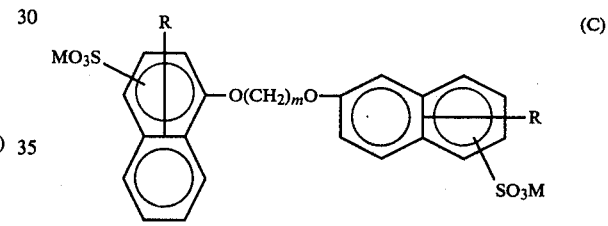

wherein R is hydrogen or a linear or branched alkyl having from 1 to 20 carbon atoms, n is an integer from 2 to 12, and M is selected from the group consisting of lithium, sodium, potassium, calcium, magnesium, zinc, aluminum, hydrogen, ammonium, and substituted ammonium ions derived from pharmaceutically acceptable organic amines, provided further that R and n are so selected that the weight percent of the SO3M groups is between about 18 and about 35, in a pharmaceutically acceptable oral hygiene vehicle compatible with said compound of structure (A), (B) or (C).

3. The composition of claim 2 wherein M is a metal selected from the group consisting of potassium, lithium, sodium, calcium, magnesium, zinc and aluminum.

4. A method of preventing attachment of dental plaque to teeth comprising periodically applying to the teeth a composition of claim 2.

5. The method of claim 4 wherein said composition is applied from about 1 to about 3 times per day.

* * * * *